US010098735B2

(12) United States Patent
Lei et al.

(10) Patent No.: US 10,098,735 B2
(45) Date of Patent: Oct. 16, 2018

(54) COMPRESSION DEVICE FOR ARTIFICIAL VALVE REPLACING DEVICE

(71) Applicant: Venus Medtech (Hangzhou) Inc., Hangzhou, Zhejiang (CN)

(72) Inventors: Rongjun Lei, Hangzhou (CN); Zhenjun Zi, Hangzhou (CN)

(73) Assignee: Venus Medtech (Hangzhou), Inc., Hangzhou (CN)

( * ) Notice: Subject to any disclaimer, the term of this patent is extended or adjusted under 35 U.S.C. 154(b) by 66 days.

(21) Appl. No.: 14/418,582

(22) PCT Filed: Aug. 6, 2013

(86) PCT No.: PCT/CN2013/080868
§ 371 (c)(1),
(2) Date: Jan. 30, 2015

(87) PCT Pub. No.: WO2014/026555
PCT Pub. Date: Feb. 20, 2014

(65) Prior Publication Data
US 2015/0190228 A1    Jul. 9, 2015

(30) Foreign Application Priority Data

Aug. 14, 2012  (CN) .......................... 2012 1 0288463

(51) Int. Cl.
*B23P 19/02* (2006.01)
*A61F 2/24* (2006.01)
*A61F 2/95* (2013.01)

(52) U.S. Cl.
CPC .... *A61F 2/2427* (2013.01); *A61F 2002/9522* (2013.01); *Y10T 29/53657* (2015.01)

(58) Field of Classification Search
CPC ........... A61F 2/2427; A61F 2002/9522; Y10T 29/53657

(Continued)

(56) References Cited

U.S. PATENT DOCUMENTS 3,055,692 A * 9/1962 Kausche ................ A01G 25/00
269/212
3,653,115 A * 4/1972 Perkins .................... F16L 1/09
254/29 R (Continued)

FOREIGN PATENT DOCUMENTS

| CN | 102805676 | 12/2012 |
| WO | WO 01/21076 | 3/2001 |
| WO | WO 02/11646 | 2/2002 |

*Primary Examiner* — David Bryant
*Assistant Examiner* — Nirvana Deonauth
(74) *Attorney, Agent, or Firm* — Raymond Sun

(57) ABSTRACT

The present invention discloses a compression device for artificial valve replacing device that comprises at least two clamp unit blocks connecting with each other in sequence and enclosing a compressing channel. The compression device further comprises a guide structure for leading all clamp unit blocks to retract towards the center of the compressing channel. In this invention, when the artificial valve replacing device is placed in the compressing channel, the inner wall of the compressing channel props against the peripheral wall of the artificial valve replacing device. When the clamp unit blocks are retracting towards the center of the compressing channel under the action of outside force, the inner wall of the compressing channel applies the force directing to the center of the compressing channel. The device has the low manufacturing cost and is convenient to clean due to the simple structure, fully satisfying the requirements for operation sanitation in use. Therefore, the production and maintenance costs are reduced and the expense shifted to consumers is lowered.

10 Claims, 6 Drawing Sheets

(58) Field of Classification Search
USPC .......................... 29/235, 237, 261, 278, 271
See application file for complete search history.

(56) References Cited

U.S. PATENT DOCUMENTS

| | | | | |
|---|---|---|---|---|
| 3,803,699 | A * | 4/1974 | Rizzo | B25B 27/10 |
| | | | | 29/237 |
| 5,697,135 | A * | 12/1997 | Dischler | B21D 39/04 |
| | | | | 29/237 |
| 6,311,789 | B1 * | 11/2001 | Saxman | E21B 19/18 |
| | | | | 175/57 |
| 6,387,117 | B1 | 5/2002 | Arnold, Jr. et al. | |
| 6,769,161 | B2 | 8/2004 | Brown et al. | |
| 7,415,861 | B2 | 8/2008 | Sokel | |
| 8,490,261 | B2 * | 7/2013 | Frenken | B21D 39/046 |
| | | | | 285/382.1 |
| 2005/0125978 | A1 * | 6/2005 | Frenken | B21D 39/046 |
| | | | | 29/237 |
| 2011/0056064 | A1 | 3/2011 | Malewicz et al. | |
| 2011/0175270 | A1 * | 7/2011 | Hagan | B25B 5/12 |
| | | | | 269/6 |
| 2012/0073112 | A1 * | 3/2012 | Frenken | B21D 39/048 |
| | | | | 29/525 |
| 2014/0304959 | A1 * | 10/2014 | Gilbreath | B21D 39/046 |
| | | | | 29/237 |

* cited by examiner

COMPRESSION DEVICE FOR ARTIFICIAL VALVE REPLACING DEVICE

BACKGROUND OF THE INVENTION

1. Technical Field

The present invention relates to a compression device, in particular a compression device for artificial valve replacing device.

2. Description of Related Art

When the patient's own heart valves can not open or close normally because of the variation caused by the congenital or acquired disease, the patient's health and even life will be affected. Variations of heart valves are divided into insufficient opening and insufficient closing, both of which may create greater load on heart. Whether the heart can work regularly under this load determines the replacement of the heart valve for the human. If the heart valve has to be replaced for the patient, the existing method is to carry out the valve replacement surgery, which means the surgeon performs the thoracotomy for the patient to stop the heart and connects the patient onto the cardiopulmonary circulatory system in vitro. The surgeon then cuts off the diseased heart valve, sews the artificial replacement valve on the very place, and finally sutures the heart and the chest. This is a quite traumatic surgical procedure, involving certain risk of death and a long time to recover. Due to the surgical trauma, many patients can not afford it or undergo the surgery even though they are in need of replacement of heart valves.

To lower the risk of surgery. U.S. Pat. No. 5,370,685, U.S. Pat. No. 5,411,552, U.S. Pat. No. 5,718,725 and U.S. Pat. No. 6,425,916 discloses the method for non-thoracic surgery for replacing heart valve and the artificial heart valve replacement device that can reduce the trauma and pain caused by thoracotomy. The artificial valve replacement device comprises the nickel-titanium shape-memory alloy stent directed into the body vascular cavity by means of catheter tube insertion technology. Before entering human body, the stent has to be compressed and placed into the transport sheath catheter so as to adapt to the vessel diameter and avoid scratching the vascular wall.

In the patent entitled "Prosthetic Valve Crimping Device" with Chinese patent authorization notice number of CN101257863 dated May 11, 2011, a crimping mechanism is disclosed, whereby a plurality of circumferentially arrayed wedge-shaped blocks form an equilateral polygon and peripheral closed columnar space. The compression and expansion of the equilateral polygon columnar space is achieved through each wedge-shaped block's synchronous and translational moving to the axis center. The design requires the slide and the driving structure added to the periphery of the wedge-shaped blocks to ensure its translational and synchronous movement plus the base part.

The device has high manufacturing cost and complicated structure, bringing difficulties to cleaning and sterilization; and therefore is required for disposable use, which undoubtedly creates great burden to patients. Moreover, the device has larger outside dimension, making it impossible to do martensitic transformation treatment on the nickel-titanium shape-memory alloy stent with simple cooling method (such as a flat pan filled with ice-water mixture). If the stent is compressed after becoming soft at a low temperature, such as being compressed under austenite phase, it will produce multiple radial supporting forces, causing loading problems and easy damage to the sheath catheter.

BRIEF SUMMARY OF THE INVENTION

In order to overcome deficiencies of the existing technology, the present invention provides a compression device for artificial valve replacing device which is simple in structure, easy to operate, convenient to clean and low in production cost.

The technical proposal of this invention is: A compression device for artificial valve replacing device, comprising clamp unit blocks. The number of the clamp unit blocks is at least two. The clamp unit blocks are connected with each other in sequence and enclose a compressing channel. The compression device further comprises a guide structure for leading all clamp unit blocks to retract towards the center of the compressing channel.

In a further aspect of the invention: the said clamp unit blocks comprise a connecting portion and comb-shaped connecting arms fixed on both sides of the connecting portion; the clamp unit blocks are glidingly connected with each other by adjacent connecting arms.

With the above technical proposal, the connecting arms on the clamp unit blocks are in comb shape, comprising a plurality of parallel unit sheets. The comb-shaped connecting arms on two clamp unit blocks are interleaved and crossed in a staggered row, facilitating the inflow and outflow of freezing liquid through the compressing channel, and improving the cooling effect on the artificial valve replacing device.

In a further aspect of the invention, the said connecting arms comprise a plurality of sheet-like comb teeth axially arranged along the compressing channel.

With the above technical proposal, the comb-shaped structure is formed by a plurality of sheet-like comb teeth arranged in parallel to each other and axially along the compressing channel. With such arrangement, the side of the clamp unit block that faces to the compressing channel comprises the space between each parallel comb tooth, and such space ensures the free flow of freezing liquid into and out of the compressing channel. When this invention performs crimping operation on the artificial valve replacing device, the entire compression device needs to be submerged in the container filled with freezing liquid so that the freezing liquid can flow into the compressing channel through the space and allow the artificial valve replacing device to have direct contact with it to get fully cooled and softened, and to reduce resistance that each clamp unit block has against the artificial valve replacing device during the crimping and retracting process.

In a further aspect of the invention: the said connecting portion and the comb-shaped connecting arms fixed on two sides of the connecting portion are in an integrated structure, and the clamp unit blocks are the same in shape.

With the above technical proposal, the connecting portion and the connecting arms are of integrated structure; in other words, a single clamp unit block can be directly molded by die casting. Because each clamp unit block is identical in shape, they can be molded by the same die. In this way, the cost of manufacturing and maintaining dies can be lowered and the productivity can be improved.

In a further aspect of the invention, guide grooves are corresponding provided between the sliding fit connecting arms, each of the guide grooves is provided with an anti-off plug, the guide groove and the anti-off plug form the guide structure.

With the above technical proposal, the corresponding position of guide grooves indicates two guide grooves are opened at the sliding fit connecting arms on the two adjacent clamp unit blocks and the two guide grooves are overlapped or overlaid. An anti-off plug is provided in the overlapped or overlaid guide grooves. The anti-off plug plays the role of preventing the disconnection of the adjacent clamp unit blocks as well as guiding and limiting the movement of the two clamp unit blocks. Because of the movement limitation by the anti-off plug, the guide grooves on the two connecting arms will stay staggered away when the two connecting arms are away from each other. However, because of the connecting and guiding role of the anti-off plug, the two connecting arms are not disconnected though they keep away from each other, ensuring the relative movement between the two adjacent clamp unit blocks without separation.

In a further aspect of the invention: an axial cross-section of the said compressing channels is an equilateral polygon.

With the above technical proposal, when the artificial valve replacing device is placed in the compressing channel, the inner wall of the compressing channel props against the peripheral wall of the artificial valve replacing device. When the clamp unit blocks are retracting towards the center of the compressing channel under the action of the outside force, the inner wall of the compressing channel applies the force directing to the center of the compressing channel. Since the axial cross-section of the compressing channel is an equilateral polygon, the force applied to the peripheral wall of the artificial valve replacing device is equally distributed in the circumferential direction of the artificial valve replacing device with equal magnitude, thereby ensuring the peripheral wall of the artificial valve replacing device is retracting simultaneously towards the center of the compressing channel under the force without inside recess at any point caused by uneven force applied. Also, the equilateral polygon formed by the compressing channel is a dynamic one and remains an equilateral polygon in the dynamic changing process of the compressing channel despite how the compressing channel narrows to the center when each clamp unit block is retracting towards the center.

In a further aspect of the invention: the number of the said clamp unit blocks is N, and the anti-off plug comprises N−1 or N anti-rotation sliders.

With the above technical proposal, anti-off plugs can be divided into two kinds of structure: columnar and blocky. Anti-off plugs in columnar shape are briefly called anti-off column, which can guide the direction between the two adjacent clamp unit blocks but can not limit the rotational degree of freedom between the two clamp unit blocks. Therefore, if limited by anti-off column, the two clamp unit blocks may suffer relative rotation. Anti-off plugs in blocky shape are called anti-rotation sliders. When anti-rotation sliders are inserted in the guide grooves, the conflict between the peripheral wall of the anti-rotation sliders and the inner wall of the guide grooves only allows the anti-rotation sliders to slide within the guide grooves instead of rotating. Therefore, the rotational degree of freedom between the two clamp unit blocks is limited by anti-rotation sliders and the two clamp unit blocks can't have relative rotation. As restricted by anti-rotation sliders, two adjacent clamp unit blocks can only slide along the direction of guide grooves with only one sliding direction, and are limited in their movement. In particular, should two of the anti-off plugs take the form of anti-off column, the compressing channel would be divided into two movable cells by the line between these two anti-off columns. At the point where each anti-off column is located, there is one rotational degree of freedom and one translational degree of freedom along the direction of guide groove, which means the two movable cells as a whole can have relative rotation as influenced by two rotational degrees of freedom. Therefore, the retracting of the compressing channel on the compression device has more than one movement trail. If the number of the retracting trail is more than one, the precision and accuracy of the retracting of the compressing channel will be affected, and the quality of the artificial valve replacing device after retraction will be affected too. In order to guarantee the uniqueness of the movement trail of the retracting compressing channel, the number of the anti-off plugs bearing the rotational degree of freedom can not exceed one. In other words, when the number of the clamp unit blocks is N, the least number of anti-rotation sliders is N−1. From the previous description, anti-off columns can rotate in the guide groove, which means the two clamp unit blocks if limited by anti-off columns may have relative rotation. Especially, when the outside force is applied unequally to each of the clamp unit block, it is much easier for the clamp unit blocks limited in movement by anti-off columns to have relative rotation and the axial cross-section of the compressing channel can hardly maintain the shape of an equilateral polygon in the process of retracting. As a result, the compression force by applied by the compressing channel against the peripheral wall of the artificial valve replacing device is uneven, leading to the recess of the peripheral wall and affecting the quality of the artificial valve replacing device.

In a further aspect of the invention: the number of the said clamp unit blocks is three, the anti-off plug comprises two or three anti-rotation sliders, and the guide grooves in any two guide structures are positioned an angle of 60 degrees.

With the above technical proposal, the optimal number of clamp unit blocks is three and three is also the least number of clamp unit blocks. With this number, the structure of the clamp unit blocks has been simplified to the largest extent when the crimping operation is performed on the artificial valve replacing device, and the production and maintenance cost has been reduced to some extent. The small number of clamp unit blocks makes it easier to clean them, reducing the difficulty of cleaning, thus improves the sanitation condition of the artificial valve replacing device under crimping operation. The guide grooves in any two guide structures are positioned to form an angle of 60 degrees, which means the longitudinal directions of the two guide grooves form the angel of 60 degrees. In this way, when the three clamp unit blocks are retracting towards the center of the compressing channel, the motion displacement of each keeps the same, or the retracting speed of each remains the same and the cross-section of the compressing channel maintains the shape of a dynamic equilateral polygon.

In a further aspect of the invention: the two connecting arms on the same clamp unit block form an angular slot with an angel of 120 degrees toward a side of the compressing channel.

With the above technical proposal, when the number of the clamp unit blocks is three and there is an angular slot on the side of each clamp unit block towards the compressing channel, the compressing channel enclosed by three clamp unit blocks is a regular hexagon and each angle of this hexagon is 120 degrees, which is also the angle of the angular slot. Meanwhile, the angular slot is opened along the axial direction of the compressing channel and runs along the clamp unit block. It is in the radial plane of the compressing channel. The opening angles of the angular slots are towards the center of the compressing channel and enclose a regular hexagon. The simple structure of the three clamp unit blocks and their small size enables the whole compression device to fully submerge into the freezing liquid when the artificial valve replacing device is under crimping operation. There is not much consumption of the freezing liquid and the cleaning is fairly easy and convenient.

In a further aspect of the invention: the number of the said clamp unit blocks is six.

With the above technical proposal, the increase in the number of the clamp unit blocks leads to the increase in the sides of the equilateral polygon in the compressing channel enclosed by these clamp unit blocks. When the number of the clamp unit blocks is six, the compressing channel is a regular decagon. As the crimping of the artificial valve replacing device is the result of the force applied through the inner wall of the compressing channel. In case of six clamp unit blocks, there are ten forces against the peripheral walls of the artificial valve replacing device along the circumferential direction of the compressing channel and directing to the center of the compressing channel. The more forces applied, the more evenly the artificial valve replacing device will receive these forces in the circumferential direction, and the more stable the artificial valve replacing device is in the process of retracting. Recess in the peripheral wall of the artificial valve replacing device is unlikely to happen and the artificial valve replacing device is protected in the crimping process.

The beneficial effects of the present invention are: when the artificial valve replacing device is placed in the compressing channel, the inner wall of the compressing channel props against the peripheral wall of the artificial valve replacing device. When the clamp unit blocks are retracting towards the center of the compressing channel under the action of the outside force and the guidance of the guide structure, the inner wall of the compressing channel applies the force directing to the center of the compressing channel to the peripheral wall of the artificial valve replacing device. Compared with traditional compression devices, the present invention is simple in structure and less expensive in overall manufacturing. In addition, it is convenient to operate the present invention. When the clamp unit blocks are driven to move along the guide structure, they are retracting towards the center of the compressing channel and the inner wall of the compressing channel applies the compressing force against the peripheral wall of the artificial valve replacing device. The simple structure of the present invention also facilitates the cleaning, satisfying the requirement for sanitation. The cost of material, production and maintenance is reduced accordingly, and the expense shifted to consumers is lowered.

DETAILED DESCRIPTION OF THE INVENTION

Figure 1:
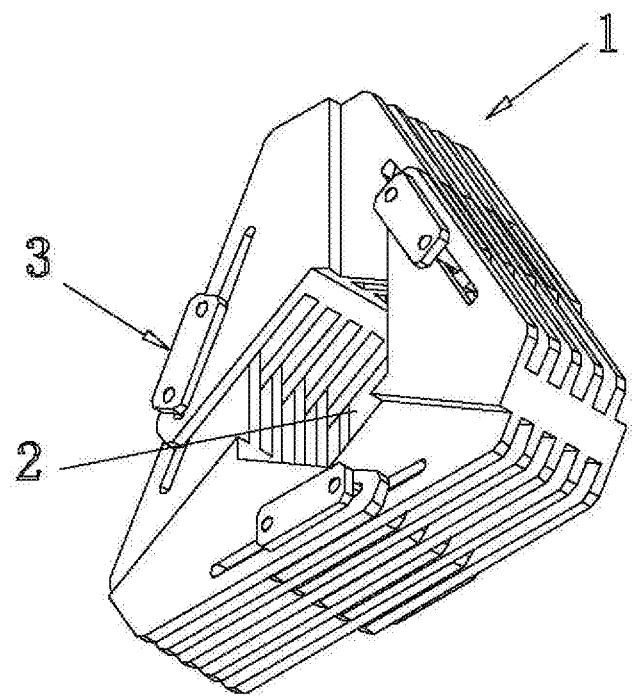
FIG. 1 is a schematic view of the Embodiment 1 according to the present invention.
Figure 2:
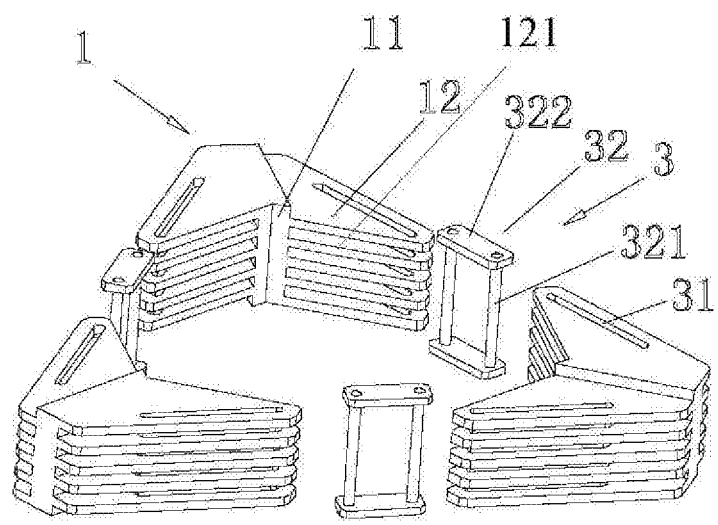
FIG. 2 is an exploded view of FIG. 1
Figure 3:
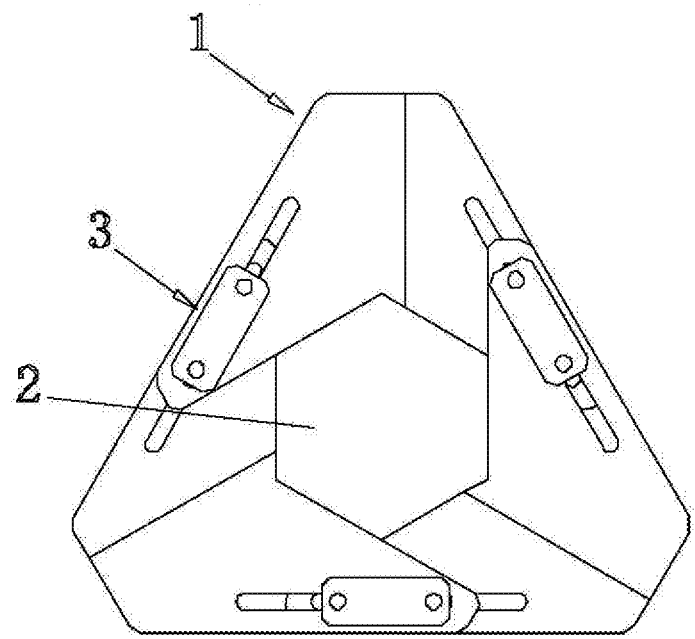
FIG. 3 is a top view of the Embodiment 1 according to the present invention
Figure 4:
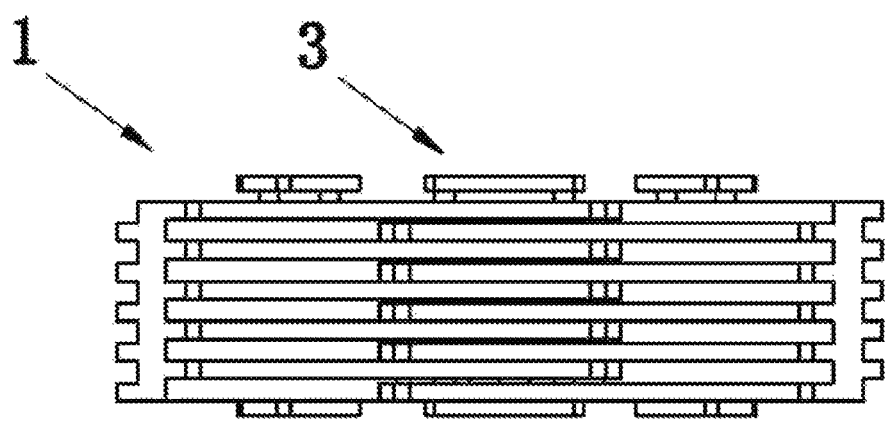
FIG. 4 is a plan view of FIG. 3.
Figure 5:
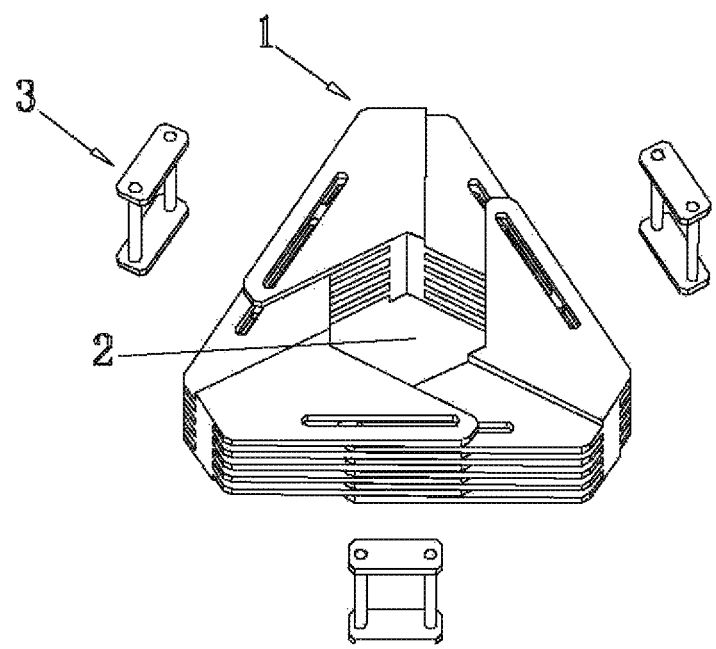
FIG. 5 is an exploded view of the Embodiment 1 from another perspective.

In the following, the present invention is described in further detail in conjunction with the attached drawings.

Embodiment 1 as shown in FIG. 1-5, there are three clamp unit blocks 1 in this embodiment. The clamp unit blocks 1 comprise the connecting portions 11 and the comb-shaped connecting arms 12 fixed on both sides of the connecting portions 11. The sheet-like comb teeth on the connecting arms 12 are axially arranged along the compressing channel 2. The three clamp unit blocks 1 are connected in sequence by connecting arms 12 to form a closed circular structure. The center of the circular structure is the compressing channel 2 and the two adjacent connecting arms 12 are interleaved, crossed and glidingly fit. The comb-shaped structure of the connecting arms 12 comprises some sheet-like parallel comb teeth 121 which are axially arranged along the compressing channel 2. The sides of the clamp unit blocks 1 that face the compressing channel comprise the space between the adjacent parallel comb teeth 121, and such space ensures the free flow of freezing liquid. When this invention performs crimping operation on the artificial valve replacing device, the freezing liquid can flow into and out of the compressing channel 2 through such space, and the artificial valve replacing device can have direct contact with the freezing liquid. In this way, the artificial valve replacing device gets cooled as soon as possible. After the softening of the shape-memory alloy stent, the clamp unit blocks 1 begin to compress the artificial valve replacing device. Connecting portions 11 and connecting arms 12 are in an integrated structure while the three clamp unit blocks 1 are in the same shape and same size. Therefore, they can be molded by die casting.

To control the movement of each clamp unit block 1, a guide structure 3 is provided between two adjacent connecting arms 12. The entire compression device has three guide structures 3 in total to guide the clamp unit blocks 1 to retract towards the center of the compressing channel 2. Each guide structure 3 includes two guide grooves 31 on two adjacent connecting arms along the same line and the anti-off plugs 32 provided in the guide grooves 31. The two guide grooves 31 included in the same guide structure 3 are located at the two adjacent clamp unit blocks 1 and the longitudinal direction of the two guide grooves 31 is parallel. In other words, the two clamp unit blocks 1 limited by the same guide structure 3 move along the same line. Anti-off plugs 32 in the three guide structures 3 are anti-rotation sliders which include two parallel connecting rods 321 and two connecting plates 322 located at both ends of the connecting rods 321 for securing them. The width of the connecting plates 322 is greater than the opening width of guide groves 31, preventing the slip off of connecting rods 321 from their own axial direction. Two mutually parallel connecting rods 321 are located in the same plane so that the whole structure can be viewed as a bar with a rectangular axial cross-section. This guide structure can limit the relative rotation between two adjacent connecting arms 12 in the guide groove 31, and ensure that the two connecting arms 12 won't disengage in the direction of the guide groove 31.

Certainly, in accordance with the coordination between guide structures 3 in Embodiment 1, among the three anti-off plugs 32, two of them can be anti-rotation sliders and the third one can be an anti-off column with a circular axial cross-section. In this way, the three clamp unit blocks 1 can still achieve synchronous compressing or expanding the compressing channel 2 and will not cause relative rotation between any two adjacent clamp unit blocks 1.

In order to ensure that the peripheral wall of the artificial valve replacing device in the compressing channel 2 receives equal force, an angular slot 13 with an angle of 120 degrees is opened on the sides of two connecting arms 12 on the same clamp unit block 1 facing to the compressing channel 2. The edges of the vertex of the angular slot 13 are arranged along the axial direction of compressing channel 2 and run along the clamp unit block 1. In the radial plane of the compressing channel 2, the opening direction of the angular slot 13 faces to the center of the compressing channel 2. As every angular slot 13 on the clamp unit block 1 facing to the compressing channel 2 is 120°, the cross-section of the compressing channel 2 is a regular hexagon, ensuring the peripheral wall of the artificial valve replacing device to receive forces evenly. The simple structure of the three clamp unit blocks and their small size enables the whole compression device to fully submerge into the freezing liquid when the artificial valve replacing device is under crimping operation. There is not much consumption of the freezing liquid and the cleaning is fairly easy and convenient.

In order to ensure the balanced retracting speed of the compressing channel 2, the angle between the guide grooves 31 in any two guide structures 3 is set at 60 degrees, which refers to the angle formed along the longitudinal directions of the two guide grooves 31 in any two guide structures 3. In this way, when the three clamp unit blocks 1 are retracting towards the center of the compressing channel 2, the motion displacement of each clamp unit block 1 keeps the same within unit time or the retracting speed of the compressing channel 2 remains the same. When the clamp unit blocks 1 are retracting towards the center, the compressing channel 2 is retracting in the same direction, but remains the shape of a regular hexagon in the dynamic changing process. Since the axial cross-section of the compressing channel 2 is a regular hexagon, the force applied to the peripheral wall of the artificial valve replacing device is equally distributed in the circumferential direction of the artificial valve replacing device with equal magnitude, thereby ensuring the peripheral wall of the artificial valve replacing device is retracting simultaneously towards the center of the compressing channel 2 under the force without inside recess at any point caused by uneven force applied.

In the present invention, when the artificial valve replacing device is placed in the compressing channel 2, the inner wall of the compressing channel 2 props against the peripheral wall of the artificial valve replacing device. When the clamp unit blocks 3 are simultaneously retracting towards the center of the compressing channel 2 under the action of the outside force, the inner wall of the compressing channel 2 applies the force directing to the center of the compressing channel 2. Compared with traditional compression devices, the present invention is simple in structure and less expensive in overall manufacture. In addition, it is more convenient to operate the present invention. When the clamp unit blocks 1 are driven to move along the guide structure, they are retracting towards the center of the compressing channel 2 automatically and the inner wall of the compressing channel 2 applies the compressing force directing to the center of the compressing channel 2 against the peripheral wall of the artificial valve replacing device. The simple structure of the present invention also facilitates the cleaning, satisfying the requirement for sanitation. The cost of material, production and maintenance is reduced accordingly, and the expense shifted to consumers is lowered. The simple structure of the three clamp unit blocks 1 and their small size enables the whole compression device to frilly submerge into the freezing liquid when the artificial valve replacing device is under crimping operation. There is not much consumption of the freezing liquid and the cleaning is fairly easy and convenient. The small size of the device allows the hand to press from outside of the clamp unit block 1 to the center of the compressing channel 2 and to separate out the three clamp unit blocks 1. Easy to operate and small in occupation space, it is convenient to operate the device in the operating room.

Figure 6:
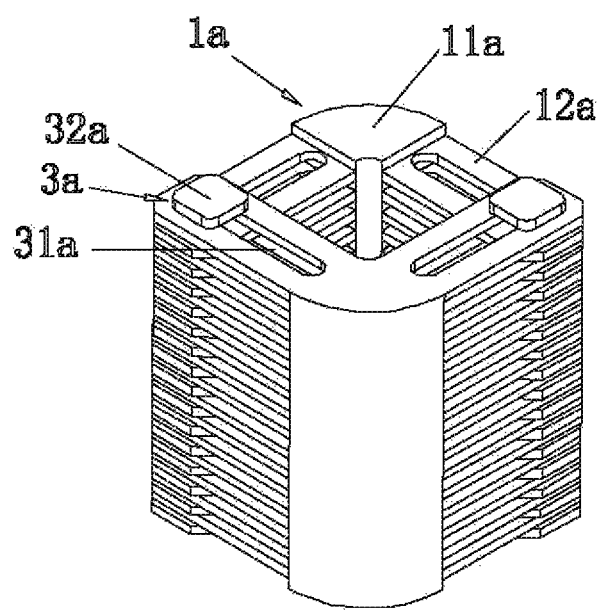
FIG. 6 is a schematic view of the Embodiment 2 of the present invention.
Figure 7:
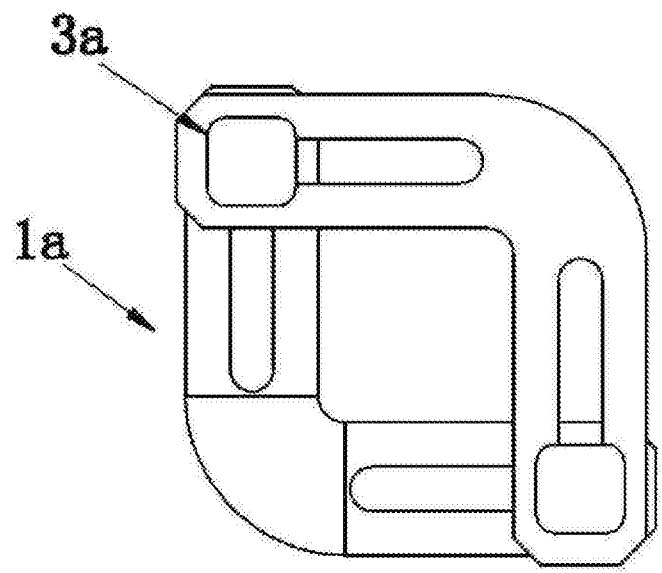
FIG. 7 is a top view of the Embodiment 2 of the present invention.
Figure 8:
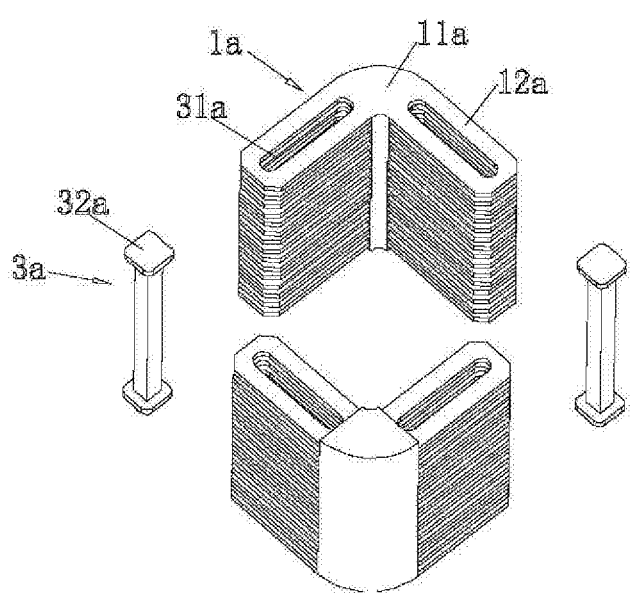
FIG. 8 is an exploded view of FIG. 6.

Embodiment 2 as shown in FIG. 6-8, there are two clamp unit blocks 1a in this embodiment. The clamp unit block 1a comprises connecting portions 11a and comb-shaped connecting arms 12a fixed on both sides of the connecting portions 11a. The sheet-like comb teeth on connecting arms 12a are axially arranged along the compressing channel 2a. The two clamp unit blocks 1a are connected in sequence by connecting arms 12a to form a closed circular structure. The center of the circular structure is the compressing channel 2a and the two adjacent connecting arms 12a are interleaved, crossed and glidingly fit.

To control the movement of the clamp unit block 1a, a guide structure 3a is provided between two adjacent connecting arms, guiding the clamp unit blocks 1a to retract towards the center of the compressing channel 2a. There are two guide structures 3a, and each of them comprises two guide grooves 31a at the corresponding positions on two adjacent connecting arms 12a and the anti-off plugs 32a provided in the guide grooves 31a. The two corresponding guide grooves 31a on two adjacent connecting arms are arranged perpendicular to each other. Two anti-off plugs 32a are block-shaped anti-rotation sliders with square axial cross-section. At both ends of the anti-rotation sliders, there are stopper plates, preventing anti-rotation sliders from escaping the guide groove 31a along their own axial direction. The anti-rotation sliders not only limit the two adjacent connecting arms 12a to move along guide grooves 31a, but also prevent the relative rotation between two adjacent connecting arms 12a.

Certainly, in accordance with the coordination between guide structures 3a in Embodiment 2, one of the two anti-off plugs 32a is an anti-rotation slider and the other is an anti-off column with a circular axial cross-section. In this way, the two clamp unit blocks 1a can still achieve synchronous compressing or expanding the compressing channel 2 under guide structures 3a.

In order to ensure that the peripheral wall of the artificial valve replacing device in the compressing channel 2a receives equal force, an angular slot 13a with an angle of 90 degrees is opened on the sides of two connecting arms 12a on the same clamp unit block 1a facing to the compressing channel 2a. The opening of the angular slot 13a is oriented to the center of the compressing channel 2a. Two angular slots 13a create the square structure of the compressing channel 2a. The two clamp unit blocks 1a are driven by the outside force to retract to the center of the compressing channel 2a. The four side walls of the compressing channel 2a prop against the peripheral wall of the artificial valve replacing device in it. The peripheral wall of the artificial valve replacing device then receives four pressing forces perpendicular to the side walls of the compressing channel 2a and retracts towards the center of the compressing channel 2a under the action of the four forces. In this way, the artificial valve replacing device achieves contraction and retraction.

Figure 9:
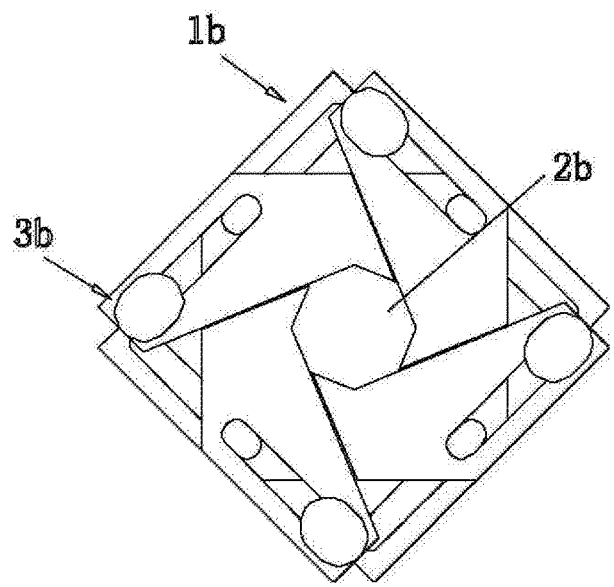
FIG. 9 is a top view of the retracting state of the Embodiment 3 according to the present invention.
Figure 10:
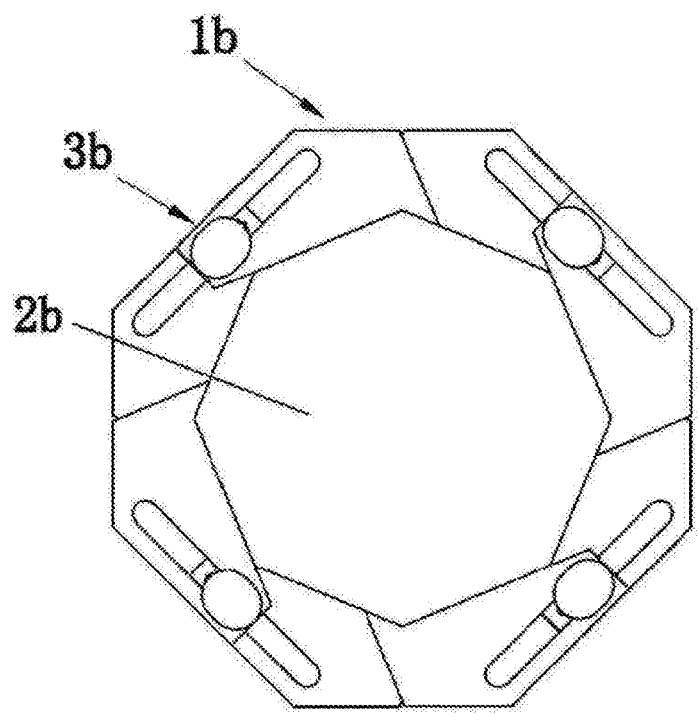
FIG. 10 is a top view of the expanding state of the Embodiment 3 of according to the present invention.
Figure 11:
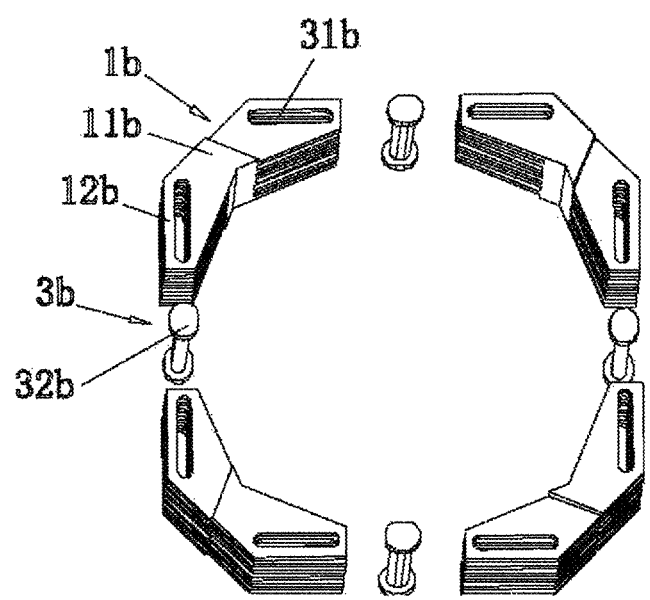
FIG. 11 is an exploded view of the Embodiment 3 according to the present invention.

Embodiment 3 as shown in FIG. 9-11, there are four clamp unit blocks 1b in this embodiment. The clamp unit blocks 1b comprises connecting portions 11b and the comb-shaped connecting arms 12b fixed on both sides of the connecting portions 11b. The sheet-like comb teeth on connecting arms 12b are axially arranged along the compressing channel 2b. The four clamp unit blocks 1b are connected in sequence by connecting arms 12b to form a closed circular structure. The center of the circular structure is the compressing channel 2b and the two adjacent connecting arms 12b are interleaved, crossed and glidingly fit.

To control the movement of the clamp unit blocks 1b, a guide structure 3b is provided between two adjacent connecting arms, guiding the clamp unit blocks 1b to retract towards the center of the compressing channel 2b. There are four guide structures 3b, and each of them comprises two guide grooves 31b at the corresponding positions on two adjacent connecting arms 12b and anti-off plugs 32b provided in the guide grooves 31b. The anti-off plugs 32b are block-shaped anti-rotation sliders with square axial cross-section. At both ends of the anti-rotation sliders, there are stopper plates preventing anti-rotation sliders from escaping guide grooves 31b along their own axial direction. Two guide grooves 31b in the same guide structure 3b stand in the same line. The anti-off plugs 33b provided in the corresponding two guide grooves 31b guide the two adjacent clamp unit blocks 1b to move along the line where the guide grooves 31b are located. The four lines where the guide grooves 31b in the four guide structures 3b are located form a rectangular along the circumferential direction of the compressing channel 2b. When four clamp unit blocks 1b move along the line where four guide grooves 31b are located, the compressing channel 2b will retract to the center.

In order to ensure that the peripheral wall of the artificial valve replacing device in the compressing channel 2b receives equal force, an angular slot 13b with an angle of 135 degrees is opened on the sides of two connecting arms 12b on the same clamp unit block 1b facing to the compressing channel 2b. The opening of the angular slot 13b is oriented to the center of the compressing channel 2b. Eight angular slots 13b create the regular octagon structure. The two clamp unit blocks 1b are driven by the outside force to retract to the center of the compressing channel 2b which takes the shape of a regular octagon. Eight side walls of the compressing channel 2b prop against the peripheral wall of the artificial valve replacing device in it. The peripheral wall of the artificial valve replacing device then receives eight pressing forces perpendicular to the eight side walls of regular octagon-shaped compressing channel 2b and retracts towards the center of the compressing channel 2b under the action of the eight forces.

In the present invention, if the number of the clamp unit blocks is five, six or even more, correspondingly, an angular slot is set on the side of the clamp unit block facing to the compressing channel. If the number of clamp unit blocks is set as N, the angle of the angular slot will be (180-180/N) degrees and the compressing channel will take the shape of a 2N-sided regular polygon. There is a guide structure between any two clamp unit blocks, guiding the clamp unit blocks to retract towards the center of the compressing channel so as to make sure the clamp unit blocks are pressing against the peripheral wall of the artificial valve replacing device to help it achieve crimping.

The invention claimed is:

1. A compression device for artificial valve replacing device, comprising clamp unit blocks, wherein the number of the clamp unit blocks is at least two; the clamp unit blocks are connected in sequence and enclose a compressing channel; the compression device further comprises guide structures for leading all the clamp unit blocks to retract towards a center of the compressing channel; the clamp unit block comprises a connecting portion and sliding fit comb-shaped connecting arms fixed on both fides of the connecting portion, with the sliding fit comb-shaped connecting arms of adjacent clamp block units sliding linearly within guide grooves as they interleave during retraction of the clamp unit blocks, and wherein the clamp unit blocks are connected to form a continuous circumferential aid surrounding structure that surrounds the compressing channel when the clamp unit blocks are in both a compressed position and a non-compressed position.

2. The compression device for artificial valve replacing device according to claim 1, wherein the sliding fit comb-shaped connecting arms comprises a plurality of sheet-shape comb teeth axially arranged along the compressing channel.

3. The compression device for artificial valve replacing device according to claim 2, wherein the connecting portion and the sliding fit comb-shaped connecting arms fixed on two sides of the connecting portion are in an integrated structure, and the clamp unit blocks have the same shape.

4. The compression device for artificial valve replacing device according to claim 1, wherein the guide grooves are correspondingly provided between the sliding fit comb-shaped connecting arms, each of the guide grooves is provided with an anti-off plug, the guide groove and the anti-off plug form the guide structure.

5. The compression device for artificial valve replacing device according to claim 4, wherein an, axial cross-section of the compressing channel is an equilateral polygon.

6. The compression device for artificial valve replacing device according to claim 4, wherein the number of the clamp unit blocks is N, the anti-off plug comprises N–1 or N anti-rotation sliders.

7. The compression device for artificial valve replacing device according to claim 6, wherein the number of the clamp unit blocks is three, the anti-off plug comprises two or three anti-rotation sliders, and the guide grooves in any two guide structures are positioned to from an angle of 60 degrees.

8. The compression device for artificial valve replacing device according to claim 6, wherein the number of the clamp unit blocks is six, and two of the sliding fit comb-shaped connecting arms on the same clamp unit block form an angular slot with an angle of 120 degrees toward a side of the compressing channel.

9. The compression device for artificial valve replacing device according to claim 2, wherein guide grooves are correspondingly provided between the sliding fit comb-shaped connecting arms, each of the guide grooves is provided with an anti-off plug, the guide groove and the anti-off plug form the guide structure.

10. The compression device for artificial valve replacing device according to claim 3, wherein guide grooves are correspondingly provided between the sliding fit comb-shaped connecting arms, each of the guide grooves is provided with an anti-off plug, the guide groove and the anti-off plug form the guide structure.

\* \* \* \* \*